(12) United States Patent
Farrusseng et al.

(10) Patent No.: US 7,893,002 B2
(45) Date of Patent: Feb. 22, 2011

(54) OXYGEN CONDUCTING MEMBRANES, PREPARATION METHOD THEREOF, AND REACTOR AND METHOD USING SAME

(75) Inventors: David Farrusseng, Caluire (FR);
Claude Mirodatos, Lyons (FR);
Michael Rebeilleau, Lyons (FR); André Van Veen, Villeurbanne (FR); Simon Rushworth, Irby (GB); Jean-Luc Rousset, Lyons (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 441 days.

(21) Appl. No.: 10/569,554

(22) PCT Filed: Aug. 19, 2004

(86) PCT No.: PCT/FR2004/002163

§ 371 (c)(1),
(2), (4) Date: Nov. 2, 2006

(87) PCT Pub. No.: WO2005/023402

PCT Pub. Date: Mar. 17, 2005

(65) Prior Publication Data
US 2007/0151857 A1    Jul. 5, 2007

(30) Foreign Application Priority Data

Aug. 28, 2003  (FR) .................................. 03 10258

(51) Int. Cl.
*B01J 20/28* (2006.01)
*B01D 53/22* (2006.01)
*B01D 61/42* (2006.01)
*C01B 13/00* (2006.01)
*C01B 3/08* (2006.01)

(52) U.S. Cl. ................. 502/4; 96/4; 204/639; 423/579; 423/657; 423/658
(58) Field of Classification Search ................. 96/4; 204/639; 502/328; 429/19, 46; 423/579, 423/657, 658; 205/742; *C25B 1/04*
See application file for complete search history.

(56) References Cited

U.S. PATENT DOCUMENTS 4,791,079 A * 12/1988 Hazbun ........................ 502/4

(Continued)

FOREIGN PATENT DOCUMENTS

EP       0 663 231        7/1995

(Continued)

OTHER PUBLICATIONS

"Oxygen permeation study in a tubular Ba0.5Sr0.5Co0.8Fe0.2O3-δ oxygen permeable membrane" Weishen Yang State Key Laboratory of Catalysis, Dalian Institute of Chemical Physics, Chinese Academy of Sciences, Jul. 22, 2002.*

(Continued)

*Primary Examiner*—Jessica L Ward
*Assistant Examiner*—Alexander Polyansky
(74) *Attorney, Agent, or Firm*—Young & Thompson (57) ABSTRACT

The invention relates to an oxygen conducting membrane includes a dense, mixed-conducting, multi-metallic oxide membrane having one surface which is coated with dispersed particles based on noble metals or magnesium oxide.

16 Claims, 7 Drawing Sheets

U.S. PATENT DOCUMENTS 6,187,157 B1 * 2/2001 Chen et al. ............... 204/296
2005/0026006 A1 * 2/2005 Haile et al. ............... 429/13

FOREIGN PATENT DOCUMENTS

EP 0 766 330 4/1997
EP 0 908 227 4/1999

OTHER PUBLICATIONS

Database WPI Week 200344 Derwent Publications Ltd., London, GB; AN 2003-457993 XP002288952 & CN 1 403 196 A (HUANG Z) Mar. 19, 2003 abstract.

Haihui Wang et al: Chem. Commun., 2002, p. 1468-1469, XP001166951 cited in the application abstract.

Z. Shao et al: "Investigation of the permeation behavior and stability of a $Ba_{0.5}Sr_{0.5}Co_{0.8}Fe_{0.0.2}O_3$(delta) oxygen membrane" Journal of Membrane Science, vol. 172, No. 1-2, 2000, p. 177-188, XP001166952 Amsterdam, NL cited in the application abstract.

Hiromichi Sakamoto et al.: Science and Technology of Advanced Materials, Jan. 20, 2003, pp. 69-76, XP008041732 cited in the application the whole document.

J.L. Rousset etal.: Physical Review B, vol. 58, No. 4, Jul. 15, 1998, pp. 2150-2156, XP008041798 cited in the application the whole document.

* cited by examiner

OXYGEN CONDUCTING MEMBRANES, PREPARATION METHOD THEREOF, AND REACTOR AND METHOD USING SAME

BACKGROUND OF THE INVENTION

1. Field of the Invention

The invention relates to membranes which have electron and oxygen ion conducting properties, the method of preparation thereof and the applications thereof, in particular for the oxidative dehydrogenation of alkanes into alkenes.

2. Description of the Related Art

Oxidative dehydrogenation methods which allow saturated organic compounds to be converted into unsaturated compounds are well known. A large number of attempts to improve methods of this type have been made over recent years in order to increase in particular the conversion rates and the selectivity with regard to the desired products.

Ethylene is produced industrially by means of thermal cracking of ethane, generally in the presence of water vapour, which consists in a pyrogenic reaction of ethane at high temperatures in the order of 850° C. At the present time, the selectivity rate in terms of ethylene obtained according to this method is not higher than 80% and the yield in terms of ethylene is in the order of 60%. Although an increase in the temperature allows higher conversion rates to be achieved, this increase, however, brings about a reduction of the selectivity by promoting the formation of secondary products and their decomposition in the form of coke. The depositing of coke on the walls of the pipes of the installation principally brings about two harmful effects; on the one hand, it results in pressure drops through the pipes of the installation and, on the other hand, it offers resistance to the transfer of heat to the hydrocarbon fluid.

The formation of coke constitutes one of the main factors limiting cracking operations.

In order to attempt to overcome this limitation, methods for oxidative dehydrogenation of ethane have been developed.

There are substantially two different types of method for oxidative dehydrogenation: catalytic methods which use catalyst beds and those which use mixed conducting membranes.

The main reactions which are involved in the catalytic method are as follows:

Catalysts which allow yields for converting ethane into ethylene in the order of 45-50% to be achieved at temperatures in particular less than 700° C. have recently been described.

In this manner, Thorsteinson et al. (*J. Catal.*, 52, 1978, 116) obtained an ethylene yield of 25% with a selectivity of 90% using the catalyst MoVNbTeOx at 350° C.

Higher yields of between 44 and 50% have also been reported by Ji and Liu et al. (L. Ji, J. Liu, *Chem. Commun.*, 1996, 1203) and Velle et al. (O. J. Velle, A. Andersen, K.-J. Jens, *Catal. Today*, 6 (1990) 567) with the catalysts La/CaO, Li/La/CaO and $SrCe_{0.5}Yb_{0.5}O_{2.75}$ in a fixed bed reactor, but at temperatures in the order of from 600 to 700° C.

However, in order to achieve a yield of this type, it is necessary to operate in an oxygen-enriched atmosphere, which brings about an increase in operating costs.

Generally, although they allow the problem of coke formation to be overcome, catalytic methods for oxidative dehydrogenation are nonetheless difficult to use on an industrial scale at the present time. They have a number of disadvantages, in particular yields which are lower than those obtained using commercial methods, the consumption of the hydrogen produced, the formation of oxygenated secondary products, the inflammable nature of the reaction mixture, the requirement for oxygen enrichment and the costs which result.

The methods for selective oxidative dehydrogenation of ethane into ethylene which use dense oxygen ion conducting membranes have been found to be much more promising.

Dense conducting membranes are membranes which are capable of selectively transporting oxygen ions at temperatures which are generally higher than 600° C., most often between 700° C. and 1200° C.

The different types of dense membrane for conducting oxygen include in particular membranes composed of solid electrolyte, the ion type, and mixed ion-electron conducting membranes based on multimetal oxides.

Membranes which are formed from solid electrolyte comprise inorganic oxides, typically oxides of calcium or zirconium, which are stabilised by yttrium (YSZ) and generally have a perovskite or fluorite structure.

These membranes of the ion type transport only oxygen ions and require the application of an external electric field in order to maintain an electron flow through the membrane and thus the process of ionisation-deionisation.

Mixed ion-electron conducting membranes, in particular monophase membranes which are constituted by multimetal oxides, are, however, capable of transporting both oxygen ions and electrons without it being necessary to apply an external electric field.

The driving force which allows oxygen to be transported in mixed conducting membranes is based on a partial pressure difference of $O_2$ applied at one side and the other of the membrane. Owing to its non-porous structure, the membrane prevents any gas molecule from passing through directly. Only the oxygen ions are able to selectively migrate. The dissociation and ionisation of the oxygen is brought about in contact with the surface where the partial pressure is highest (cathode), by means of electron capture. The charge flow of the oxygen ions $O^{2-}$ is compensated for by a simultaneous flow of electrons in the opposite direction. When the oxygen ions reach the side of low partial oxygen pressure, that is to say, the side of the permeate (anode), the oxygen ions donate their electrons and recombine in order to regenerate molecular oxygen which is released into the permeation current.

These membranes, which are used as membrane reactors for the oxidative dehydrogenation of ethane, selectively transport oxygen as far as the anode where they react rapidly with ethane in order to form ethylene.

The transport of oxygen through these conduction membranes is a controlled process which is substantially dependent on two factors: the kinetic surface limitations and the limitations of volume diffusion.

The kinetic surface limitations are linked to the plurality of steps which are involved during the conversion of the oxygen molecules in a gaseous phase in the charge current into mobile oxygen ions and, conversely, of the mobile oxygen ions into oxygen molecules at the side of the permeate of the conducting membrane or during the reaction of the oxygen ions with the reactant gas.

The limitations of volume diffusion are linked to the diffusion of the oxygen ions and electrons at the inner side of the membrane.

These two limiting factors are dependent in particular on the partial pressure gradient in terms of $O_2$ at one side and the other of the membrane, the operating temperature and the thickness of the membrane.

Work has been carried out which is intended to optimise the efficiency levels of these membranes, which are advantageous in particular when used as membrane reactors for the oxidative dehydrogenation of ethane into ethylene.

A first approach involves seeking multimetal mixed conducting oxide compositions which have good intrinsic properties for transporting oxygen.

Document Haihui Wang et al., *Chem. Comm.*, 2002, 1468-1469, describes a reaction for oxidative dehydrogenation of ethane into ethylene in a membrane reactor which is constituted by $Ba_{0.5}Sr_{0.5}Co_{0.8}Fe_{0.2}O_{3-\delta}$.

The ethylene is obtained at a yield of 15%, a conversion rate of 18%, a selectivity of 90% at 650° C. and an oxygen permeation flow of $0.36$ mL·min$^{-1}$ cm$^{-2}$.

In the document H. Wang et al. (*Catalysis Letters*, 2002, vol. 84, Nos 1-2 pp. 101-106), the oxidative dehydrogenation reaction of ethane in the $Ba_{0.5}Sr_{0.5}Co_{0.8}Fe_{0.2}O_{3-\delta}$ membrane reactor is examined at 800° C. A maximum yield of 67% is obtained with a selectivity with regard to ethylene, a conversion rate and a permeation flow of oxygen of 80%, 82% and 1.6 mL cm$^{-2}$ min$^{-1}$, respectively.

Another approach involves reducing the kinetic surface limitations by associating a catalyst which promotes, for example, the dissociation of gaseous oxygen into mobile $O^{2-}$ ions.

Document EP 0 663 231 (Air Products and Chemicals, Inc.) thus describes a membrane which comprises a porous mixed conducting layer of multimetal oxide, one surface of which layer is covered with a catalyst and the other is in contact with a dense mixed conducting multimetal layer. The catalyst comprises a metal or a metal oxide which catalyses the dissociation of oxygen molecules into ions and/or the association of oxygen ions into molecular oxygen.

The two membranes which are set out by way of example in this patent application use a platinum-based catalyst at a ratio of 10 mg/cm$^2$ of surface-area. The use of an expensive precious metal in a substantial quantity as a catalyst renders the use of these membranes on an industrial scale improbable.

Document WO 99/21649 describes a catalytic membrane reactor which comprises an oxidation zone and a reduction zone which are separated by a membrane which is impermeable to gases, and which has an oxidation surface in contact with the oxidation zone and a reduction surface which is in contact with the reduction zone, a layer of adhesive catalyst on the oxidation surface of the membrane and, optionally, a three-dimensional catalyst in the oxidation zone. However, the catalysts are in the form of a continuous coating or layer.

Furthermore, only the catalysts $La_{0.8}Sr_{0.2}MnO_3$ and cermet of Ni on $La_{0.8}Sr_{0.2}MnO_3$ are actually envisaged. There is no mention anywhere of dispersed particles based on magnesium or noble metals.

These membranes are difficult to use and attempts have been made to produce membranes which are effective, less costly and in particular, much easier to use.

SUMMARY OF THE INVENTION

Surprisingly, it has now been discovered that, by dispersing a small quantity of catalyst based on magnesium oxide or noble metals in the form of particles at the surface of a mixed conducting membrane of multimetal oxide, it was possible to obtain less costly membranes which have high rates of conversion and selectivity.

More particularly, it has been shown that this modification of the surface of the membrane allows the flow of oxygen and/or the catalytic yield to be significantly increased, and/or the operating temperature conditions to be reduced. By way of example, the operating temperature conditions can be reduced by from 10 to 20%, which may represent approximately a hundred degrees.

This temperature reduction has a number of advantages. In addition to the reduction in the operating cost which a temperature reduction of approximately a hundred degrees represents for industrial production, this allows the problems of corrosion in the region of the reactor to be substantially reduced, and also offers a wider selection of materials for the construction of the reactor itself.

It also allows the use of a larger number of reactions to be envisaged, in particular those which require high temperatures, such as the partial oxidation of light alkanes.

In a particularly advantageous manner, it was found that placing a dense mixed conducting membrane of multimetal oxide in contact with dispersed particles based on magnesium oxide or noble metal modifies the redox properties of the membrane.

Without wishing to be limited to any one theory, it is considered that particles based on magnesium oxide or noble metals dispersed on the oxidation surface (or anode) of the membrane may promote the recombination of oxygen ions into $O_2$, then the desorption of the molecules of $O_2$.

Furthermore, the presence of the dispersed particles based on magnesium oxide or noble metals on one of the surfaces of the membrane allows the thermal stability of the resulting membrane to be increased. The membranes are thus found to be much more stable, in particular in terms of the mechanical and thermal stresses to which they are subjected under the operating conditions, retaining their structural integrity for a longer period of time.

One of the objects of the present invention is to provide mixed conducting membranes of multimetal oxides which are modified at the surface and which have an improved flow in terms of oxygen in comparison with bare membranes.

According to one advantageous feature of the invention, the composite membranes according to the invention allow an increase of the permeation flow of the oxygen, generally of between 5 and 20%, and advantageously in the order of 30%.

Another object of the present invention is to provide membranes which have high catalytic activity at lower operating temperatures.

In the context of the present description, "high catalytic activity" is intended to refer to a level of activity which allows yields to be reached which are greater than 60%, preferably greater than 70%, and more preferably greater than 80%. By way of illustration, the membranes according to the invention allow ethane to be converted into ethylene with a yield greater than 65%.

Another object of the present invention is to provide a method for preparing these membranes. Advantageously, this is easy to implement, inexpensive and can be readily used on an industrial scale, which should promote the use and the development of the membrane reactors of the invention on an industrial scale.

Another object of the present invention is to provide membrane catalytic reactors which comprise the membranes according to the invention. Advantageously, these membrane reactors allow high levels of conversion and selectivity to be reached.

The membranes according to the invention are advantageous in a large range of methods, including in particular the separation of oxygen from a gaseous mixture or the oxidation of light hydrocarbons.

Advantageously, the membranes according to the invention have an increased permeation flow of oxygen and therefore allow the oxygen to be extracted from a gaseous mixture with a high yield at a lower temperature in comparison with oxygen conducting membranes which are bare, that is to say, which have no deposit of dispersed particles based on magnesium oxide or noble metals.

In particular, the membranes according to the invention are particularly advantageous when used as a membrane reactor for the oxidative dehydrogenation of ethane, in that they allow levels of conversion, selectivities and yields to be obtained which are higher than those described in the prior art.

Another object of the present invention is therefore to provide a method for oxidative dehydrogenation of ethane into ethylene which constitutes an advantageous alternative to the method for thermal dehydrogenation of ethane.

In addition to the high levels of conversion and selectivities, this method advantageously allows the coking problems of the method for thermal dehydrogenation to be overcome. Furthermore, the separation of the oxygen coupled with the consumption thereof in the oxidative dehydrogenation reaction brings about a number of advantages: the formation of secondary oxygenated products is limited, air, in particular at atmospheric pressure, can be used directly as a source of oxygen without it being necessary to carry out a cryogenic or other distillation operation, and the operating conditions can be controlled with no danger of explosion for the installation.

These objects and others are achieved by the invention which relates, according to a first aspect, to an oxygen conducting membrane, comprising a dense mixed conducting membrane of multimetal oxide, one of the surfaces of which membrane is coated with dispersed particles based on magnesium oxide or noble metals.

Membranes

Dense Mixed Conducting Membrane of Multimetal Oxides

In the context of the present description, the term "dense" is intended to refer to a layer which is "impermeable to gaseous fluids", i.e. which does not allow the passage of a significant quantity of a gaseous fluid through the membrane. In specific cases, a low level of permeability in terms of gases other than $O_2$ may be acceptable or inevitable. This is the case, for example, when the membrane comprises structural defects or when the sealing of the reactor is defective.

Generally, the expression "dense membrane" in the context of the present invention includes membranes which have a gas permselectivity greater than 30, and preferably greater than 100.

Dense mixed conducting membranes of multimetal oxide transport the oxygen anions and are in this respect permeable to oxygen. On the other hand, they are impermeable to the gaseous oxygen itself.

In the context of the present description, "mixed conducting" is intended to refer to a dense layer which is capable of transporting both electrons and oxygen ions in a selective manner.

The dense layer of the invention is formed from a single multimetal oxide or a mixture of two or more multimetal oxides, each multimetal oxide comprising an oxide of at least two different metals or a mixture of at least two different metal oxides, in which the multimetal oxide has electron and oxygen-ion conductivity at temperatures higher than approximately 500° C. It is also possible to refer to a solid solution of multimetal oxide.

In the context of the present description, "operating temperature" is intended to refer to a temperature at which the membrane according to the invention has a significant level of electron and oxygen-ion conductivity.

Generally, the operating temperatures are between approximately 500° C. and 1100° C. The specific temperature, and the flows of reactant gas and gas containing oxygen, are optimised in accordance with the membrane, the catalyst particles and the envisaged application. The temperature must be sufficiently high to promote the oxygen anion flow through the membrane without impairing the membrane and the catalyst particles.

The dense multimetal oxide mixed conducting layer of the invention therefore designates a membrane which has electron and oxygen-ion conductivity and the capacity to separate the oxygen from a gaseous mixture containing oxygen and one or more other volatile components using the conductivities.

According to a preferred method, the dense layer is formed from mixed oxides which have a perovskite structure.

The compounds of the perovskite type comply with the formula $ABO_3$, in which A represents an ion of an alkali metal, alkaline-earth metal or rare earth metal and B an ion of a transition metal. Ideally, they have a cubic crystalline structure which is very stable and in which the ions A are positioned at the peaks of the cubic crystalline mesh, the oxygen ions are located at the centre of each face of the cube and form an octahedron $BO_6$ with B placed at the centre of the cube. Ideal perovskite structures generally have a valency total for the ions A and B equal to 6, as in the mineral perovskite model $CaTiO_3$.

The substitution of a site A or B by another alkaline-earth metal or metal cation can produce sites which are vacant in terms of oxygen. These vacant sites allow the transport of oxygen through the crystalline network.

Examples of perovskite structure are in particular cubic perovskites, Brownmillerites, Aurivillius phases or lamellar perovskites and the like.

Preferably, the perovskite structures in the context of the present description comprise structures which have a perovskite phase greater than 90%, more preferably greater than 95% and even more preferably greater than 98%.

Preferably, the dense mixed conducting membrane refers to a compound having the general formula:

in which

A and A', which may be the same or different, each represent a metal ion or an alkaline-earth metal or a metal which is selected from the lanthanide series;

B and B', which may be the same or different, each represent a metal ion and/or a mixture of metal ions in which the metal is selected from the transition metals;

$0 \leq x \leq 1$;

$0 \leq y \leq 1$;

z is a number which renders the charge of the compound neutral and which defines the oxygen deficiency; z is thus dependent on the nature of A, A', B, B', x, y and the temperature.

A and A', which may be the same or different, preferably represent La, Ca, Sr, and/or Ba, more preferably Ba and/or Sr.

According to a specific method, it is preferable for A and A' to be different.

It is in particular preferable for A to represent Ba. A' preferably represents Sr.

According to a preferred method, B and B', which may be the same or different, represent Cr, Mn, Fe, Co, Ni and/or Cu, more preferably Co and/or Fe.

B and B' are preferably different.

B preferably represents Co.

B' preferably represents Fe.

According to a preferred aspect of the invention, x is between 0.2 and 0.8, and preferably between 0.4 and 0.6.

Preferably, y is between 0.2 and 0.8, and more preferably between 0.6 and 0.8.

Preferred mixed conducting oxides are selected from $Ba_xSr_{1-x}Co_yFe_{1-y}O_{3-z}$ where x, y and z are as defined above. In this context, it is particularly preferable for x to be between 0.4 and 0.6 and y between 0.6 and 0.8.

More preferably, the dense membrane comprises the multimetal oxide $Ba_{0.5}Sr_{0.5}Co_{0.8}Fe_{0.2}O_{3-z}$.

The dense membrane must have sufficient thickness to have a good level of impermeability to gases and a good level of mechanical stability in terms of the operational stresses in the reactor.

However, it must not have an excessive level of thickness in order not to limit the flow of oxygen ions through the membrane. Generally, the flow of oxygen ions increases when the thickness of the dense membrane is reduced to a critical value at which the desorption kinetics of the oxygen ions become limiting.

The minimum thickness of the non-supported dense membrane is preferably approximately 0.5 mm. The maximum thickness of the dense mixed conducting membrane is preferably approximately 10 mm, more preferably approximately 2 mm, and more preferably approximately 1 mm.

Membranes according to the invention preferably have a thickness of between 0.5 and 2 mm, more preferably between 0.9 and 1.6 mm, and even more preferably between 0.9 and 1.1 mm.

Conventionally, the dense mixed conducting membrane has a permeation flow relative to oxygen greater than $7.4 \times 10^{-9}$ mole cm$^{-2}$s$^{-1}$, more preferably greater than $3.7 \times 10^{-9}$, at a partial pressure difference in terms of oxygen of approximately 200 hPa under optimum operating temperature conditions.

By way of indication, the membranes described in literature generally have a thickness of from 1 to 2 mm and are characterised by a permeation flow of oxygen which varies from $10^{-7}$ to $10^{-9}$ mole cm$^{-2}$s$^{-1}$, at a partial pressure difference in terms of oxygen of approximately 200 hPa.

Catalytic Deposit

In the context of the present description, the expression "coated" is intended to mean that at least one of the surfaces of the dense membrane is directly in contact with the particles based on magnesium oxide or noble metals.

In the context of the present description, "particles" is intended to refer to particles which have a spherical or anisotropic morphology and which may or may not have a crystalline structure, and which have a mean diameter which is less than or equal to 3 μm, preferably with a narrow granulometric distribution.

In the context of the present description, "dispersed" is intended to refer to a distribution of separate particles which are distributed in a random or organised manner and which form a discontinuous deposit at the surface of the membrane, given that the zones covered by the particles represent between 10% and 80% of the surface-area of the membrane.

It should be noted that the zones of the surface of the membrane which is not covered by particles based on magnesium oxide or noble metals are bare, that is to say, they are directly exposed to the reactant gases or the gas which contains oxygen. That is to say, this modified surface comprises no other coating.

The dispersion of particles based on magnesium oxide or noble metals which are directly in contact with a dense membrane allows the formation of "triple points", that is to say, an increase in the contact surface-area between the catalyst, that is to say, the particles based on magnesium oxide or noble metals, the reactant gas and the "active" oxygen ($O_2$) at the surface of the membrane.

Advantageously, this type of deposit further allows the limitation of reabsorption phenomena of the product formed on the oxidation surface by the catalyst which may lead to the degradation thereof. This therefore advantageously becomes evident in an improvement of the selectivity, in particular in the case in which the products produced are sensitive to the action of the catalyst, such as, for example, in the case of the oxidative dehydrogenation of ethane into ethylene.

In the context of the present description, the term "particles based on magnesium oxide" generally refers to any particle which is constituted completely or partially by a magnesium oxide, the magnesium oxide at the centre of the material being present in at least one of the following forms:

in the form of magnesium oxide having the formula MgO; and/or in the form of magnesium oxide referred to as "doped", that is to say, a magnesium oxide which includes metal cations for insertion or substitution.

In a doped magnesium oxide, the magnesium cations generally remain in the majority, that is to say, the molar ratio of the quantity of magnesium relative to the total quantity of cations in the doped magnesium oxide generally remains greater than 50% by mole, most often greater than 70% and, in most cases, greater than 90% by mole.

The magnesium oxide is preferably doped using a transition metal, preferably selected from vanadium.

According to a particularly preferred aspect, the magnesium oxide is doped using vanadium, preferably using from 0.5 to 10% by weight of vanadium, more preferably using 5% by weight of vanadium.

"Particles of noble metals" are understood to be particles which are constituted substantially by a noble metal selected from Pd, Pt, Rh, Au, Ru, Ag, and Ir or an alloy thereof, the noble metal being completely or partially in reduced or oxidised form. Amongst the noble metals, Pd is particularly preferred.

The particles based on magnesium oxide or noble metals are preferably dispersed in accordance with a density of between $1.10^5$ and $1.10^7$ particles per cm$^2$ and $1.10^{12}$ and $5.10^{12}$ particles per cm$^2$, respectively.

According to a preferred method, the discontinuous deposit formed by the particles based on magnesium oxide or noble metals has a specific surface-area which varies from 30 to 50 m$^2$/g, preferably between 40 and 50 m$^2$/g at an operating temperature of 800° C.

Preferably, the particles based on magnesium oxide or noble metals have a mean diameter of between 5 nm and 3000 nm, more preferably between 5 and 50 nm, and even more preferably between 5 and 10 nm.

This mean particle size advantageously allows a large specific surface-area to be made available, that is to say, allows the contact surface between the gas and the modified membrane to be increased per unit of volume.

The percentage by weight of the deposit formed by the particles based on magnesium oxide or noble metals relative to the weight of the dense mixed conducting layer can vary between approximately 0.01 and 1%, preferably between 0.01 and 0.5%, more preferably between 0.01 and 0.1%.

Method for Preparing Membranes According to the Invention

Catalyst Based on Magnesium Oxide

According to a second aspect, the invention relates to the methods for preparing the oxygen conducting membranes defined above.

The particles based on magnesium oxide can be dispersed and deposited by chemical means at the surface of the dense layer of multimetal oxide using conventional techniques, such as the depositing of colloidal suspensions, still referred to as the sol-gel method, or depositing in a vapour phase.

According to a specific embodiment, the membranes which are coated with dispersed particles based on magnesium oxide according to the invention are prepared in accordance with the methods referred to as "sol-gel", which are known to the person skilled in the art.

For further details relating to this matter, reference can be made in particular to the thesis of Laure Albaric, University of Montpellier II, 1999.

This method comprises steps which consist in:
a. providing a mixed conducting membrane of multimetal oxide as defined above;
b. preparing a colloidal suspension based on magnesium oxide in an organic solvent;
c. placing the suspension obtained in contact with the dense mixed conducting membrane; and
d. calcining the membrane obtained.

The colloidal suspension based on magnesium oxide can be prepared according to the methods referred to as "sol-gel" methods, which are known to the person skilled in the art.

The preparation of colloidal suspension thus comprises the dissolution of the precursor of the particles based on magnesium oxide in the organic solvent, in the desired proportions. The concentration of the precursor solution is fixed in accordance with the coating which it is desirable to obtain and the agitation is generally carried out at ambient temperature until a colloidal suspension is obtained.

The precursors are preferably distilled before they are used so as to eliminate possible traces of water and condensed matter.

By way of example of precursors of particles based on magnesium oxide, it is possible to mention in particular alkoxides, hydroxides, nitrates, magnesium alkoxides, such as magnesium dimethoxide.

According to a preferred embodiment, the magnesium oxide is doped using vanadium. In this case, the colloidal suspension is prepared from an admixture of precursors based on magnesium and vanadium in the desired proportions. Preferably, a solution of magnesium alkoxide and vanadium alkoxide is prepared, preferably of magnesium dimethoxide and vanadium isopropoxide.

The organic solvents used during step b) are those which are commonly used for the preparation of colloidal suspensions and include in particular methanol, ethanol, 2-propanol.

The colloidal suspension produced in step b) is then deposited at the surface of the dense mixed conducting membrane according to the known technique of "spin-coating". In this regard, reference can be made in particular to Hiromichi Sakamoto, Jianbei Qiu and Akio Makishima, *Science and Technology of Advanced Materials*, Volume 4, Issue 1, 2003, Pages 69-76. This technique generally consists in depositing a few millimetres of colloidal suspension, for example, using a syringe, at the surface of the dense membrane, and distributing the colloidal suspension in a homogeneous manner on the surface of the membrane, placing the membrane on a support which is rotated at high speed.

The deposit is then dried in air, then in an oven at 100° C. for a length of time sufficient to eliminate the solvent.

The resulting membrane is then calcined at a temperature which is sufficient to eliminate the organic residues, generally at a temperature higher than 400° C., preferably between 800° C. and 900° C., and more preferably between 800° C. and 850° C., by means of which a membrane is obtained which is coated with dispersed particles based on magnesium oxide.

The dense mixed conducting membrane used according to this method can be prepared according to conventional methods which generally comprise:
dissolving in water metal salts which constitute the mixed conducting oxide, including in particular nitrates and chlorides, in the desired stochiometric proportions;
co-precipitating the salts from the aqueous solution by means of the addition of an organic acid, for example, citric acid;
isolating the co-precipitate by means of filtration or centrifuging;
calcining the co-precipitate in order to obtain a multimetal mixed conducting oxide;
grinding the mixed conducting oxide into the form of powder;
milling the mixed conducting oxide powder, optionally in association with additives, into the desired form; and
sintering the milled powder in order to obtain a dense ceramic mixed conducting material.

These methods, which are well known to a person skilled in the art, are suitable for the preparation of the dense mixed conducting membrane of the membranes according to the invention.

The "sol-gel" method is particularly suitable for obtaining particles of micrometric or submicrometric size and dispersing them at the surface of the membrane. The size of the particles formed can be evaluated after the particles have been deposited at the surface of the membrane by means of scanning electron microscopy and/or physisorption.

Catalyst Based on Noble Metals

Membranes which are coated with dispersed particles of noble metals according to the invention can be prepared according to the method which consists in:
a) providing a mixed conducting membrane of multimetal oxide as defined above;
b) depositing the noble metal particles by means of laser vaporisation.

The principle of the technique of laser vaporisation is set out in particular in the bibliographic reference "Ion-scattering study and Monte Carlo simulations of surface segregation in Pd—Pt nanoclusters obtained by laser vaporization of the bulk alloys", J.-L. Rousset et al., *Physical Review B,* 15 Jul. 1998, II, vol. 58, No. 4.

Advantageously, this technique allows small metal particles to be deposited with a narrow and homogeneous distribution, a controlled composition and quantity.

The size and the dispersion or density of the particles on the surface of the dense membrane can be determined by means of transmission electron microscopy and/or physisorbtion.

According to a third aspect, the invention relates to membranes which can be produced according to one of the methods defined above.

The membranes according to the invention can be prepared in different forms, suitable for a specific model of reactor, including in particular in the form of discs or tubes.

The mixed conducting membranes according to the invention are advantageously stable at temperatures of between 25° C. and 1100° C.

Membrane Reactor

According to a fourth aspect, the invention also relates to a catalytic membrane reactor which comprises an oxidation zone and a reduction zone which are separated by a membrane according to the invention.

In the following, the oxidation surface (anode) designates the surface which is in contact with the oxidation zone and the reduction surface (cathode), the one in contact with the reduction zone.

The oxidation surface preferably corresponds to that which is in contact with the dispersed particles based on magnesium oxide or noble metals.

The reduction surface is in contact with the gaseous mixture which contains oxygen. It preferably corresponds to the dense layer, which is optionally covered with a catalytic layer, and is the seat for the dissociation reactions of the molecular oxygen into oxygen ions $O^{2-}$.

This reduction surface can be optionally coated with a catalyst which promotes the reduction of matter containing oxygen, such as $O_2$, $NO_2$, $SO_2$, in order to produce oxygen anions in the region of the membrane. By way of example of catalysts of this type, it is possible to mention in particular noble metals.

Application of the Membrane Reactor

The membranes according to the invention are advantageous when used as membrane reactors for the partial or total oxidation of reduced matter, in particular hydrocarbons.

According to a fifth aspect, the invention relates to a method for oxidising a reactant gas comprising:

i) using a membrane reactor according to the invention;
ii) introducing reactant gas into the oxidation zone;
iii) introducing gas containing oxygen into the reduction zone;
iv) heating the membrane which separates the oxidation and reduction zones at an operating temperature in order to reduce the gas containing oxygen, transport the oxygen ions to the oxidation zone and oxidise the reactant gas.

The operating temperature is preferably between 500 and 800° C.

This method is preferably used for a partial oxidation of the reactant gas, such as a conversion of methane into carbon monoxide and hydrogen, or an oxidative dehydrogenation of hydrocarbons, or a controlled oxidation of hydrocarbons into oxygenated molecules.

According to a preferred embodiment, the reactant gas is a light hydrocarbon which is oxidised into alkene.

In the context of the present description, "light hydrocarbon" is intended to refer to volatile alkanes which contain from 1 to 6 atoms of carbon, including in particular methane, ethane, propane and the butanes.

Light hydrocarbon is preferably ethane or propane, preferably ethane which is oxidised into ethylene.

According to another advantageous feature, the membranes according to the invention have a level of activity for the dehydrogenation of ethane into ethylene greater than that obtained with the dense membrane which has an oxidation surface which is not modified by dispersed particles based on magnesium oxide or noble metals.

According to another aspect, the invention relates to the use of membrane reactors in order to recover oxygen from a gaseous mixture which contains oxygen.

This use comprises in particular the steps which consist in:

introducing a gaseous mixture containing oxygen into the reduction zone which is separated from the oxidation zone by the membrane according to the invention, by establishing a positive partial pressure difference between the two zones by producing an excess partial pressure of oxygen in the first compartment and/or by producing a reduced partial pressure in the second compartment;

placing the mixture containing the oxygen in contact with the reduction surface, at a temperature greater than approximately 500° C. in order to convert the gaseous mixture containing oxygen into an oxygen enriched current (permeate) on the one hand, and, on the other hand, into an oxygen-depleted current;

recovering the oxygen enriched current (permeate).

The expression "gaseous mixture containing oxygen" generally refers to gases and gaseous mixtures, one of the components of which is oxygen or an oxide. These can be reduced on the reduction surface of the membrane according to the invention. This expression includes in particular oxides of carbon, nitrogen and sulphur ($CO_x$, $NO_x$ and $SO_x$) and gaseous mixtures which comprise an oxide in the presence of an inert gas or any other gas which is non-reactive relative to the membrane.

The expression also includes mixtures of molecular oxygen ($O_2$) in other gases, for example, oxygen of atmospheric air, oxygen in the presence of an inert gas, such as He, Ar, etcetera.

The membranes according to the invention thus allow the oxygen to be separated from gaseous mixtures containing oxygen and other gases, such as $CO_2$, $H_2O$ and volatile hydrocarbons. The proportion of oxygen present in such gaseous mixtures is generally between 0.01% and 50 vol. %.

According to a preferred method, the gaseous mixture containing oxygen is atmospheric air.

In a particularly advantageous manner, the presence of the dispersed particles based on magnesium oxide or noble metals on the membranes of the invention allows the quantity of oxygen recovered to be increased on average by 20%.

BRIEF DESCRIPTION OF THE DRAWING FIGURES

Figures

Legend: Sethy, SCO$_2$, SCO, SCH$_4$ represent the selectivities in terms of ethylene, carbon dioxide, carbon monoxide and methane, respectively.

Legend: Y ethy, Y propy represent the yields in terms of ethylene and propylene, respectively.

DETAILED DESCRIPTION OF THE INVENTION

EXAMPLES

Abbreviations
HC: hydrocarbon
He: helium
$C_2H_6$: ethane
$C_2H_4$: ethylene
$C_3H_8$ propane
$F_{AIR}$, $F_{C2H6}$: flow of air or ethane, respectively Materials and Methods
 The following reagents were used:
  $Ba(NO_3)_2 Sr(NO_3)_2$, $Co(NO_3)_3.6H_2O$ $Fe(NO_3)_2.6H_2O$, EDTA, citric acid (Sigma Aldrich®)
  $Mg(OMe)_2$ (9.34 g of Mg/L in methanol) (Epichem®)
  $VO(OCH_2CH_3)_3$ (Aldrich®).

The powders obtained were characterised by means of elemental analysis and X-ray diffraction and using the BET method.

The X-ray diffraction spectra were carried out using a system device Brücker® D5005 in the 2θ range, from 3° to 80°, a step of 0.02°, a time of 1s and a radiation of Cu $K_{\alpha1+\alpha2}$=1.54184 Å.

The elemental composition was determined by means of ICP-OES using a spectroflame device.

Scanning electron microscopy operations were carried out using a device Hitach S-800. The transmission electron microscopy operations were carried out using a device JEOL 2010-200 kV.

Membrane Reactor a) Description

Figure 1:
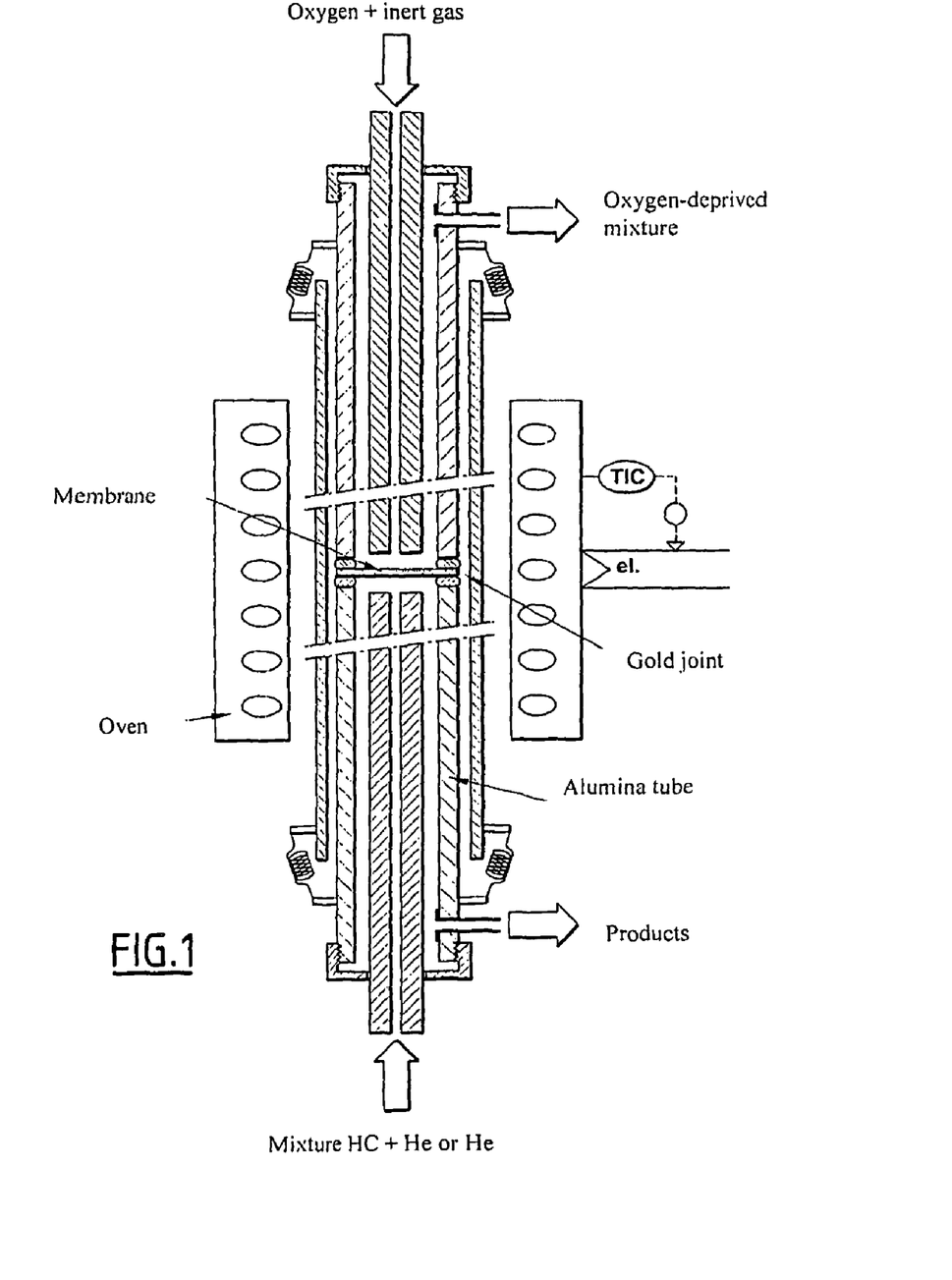
FIG. 1: Illustration of a high-temperature membrane reactor.

The oxidative dehydrogenation of ethane (DHOE) and the permeability relative to oxygen were examined using the reactor described in FIG. 1.

The discs (approximately 1 mm thick) were sealed between two dense tubes of alumina (OD 12 mm, ID 8 mm) using gold as a chemically inert sealing agent.

Furthermore, the side of the wall of the disc has been extensively covered with a gold-based adhesive in order to eliminate the radial contributions of the flow of oxygen passing through the active cross-section of 0.5 cm². The welding was carried out at the beginning of the experiments by heating to a temperature of 800° C. for one night. The side which is in contact with air was supplied with a constant total pressure adjusted to 120 kPa and a constant flow rate of 50 mL/min by using a mixed current of $O_2$ (liquid air) and $N_2$ ($N_2$ in the form of evaporated liquid air, liquid air) individually controlled by mass flow controllers (Brooks®, type 5850 TR). The side which is in contact with the fuel was supplied with a mixture of ethane (liquid air) and helium (liquid air) which is individually controlled by mass flow controllers (Brooks®, type 5850 TR) in the case of DHOE, and simply by He in the case of the permeability relative to oxygen. Two pressure sensors were installed which allow the total pressure on each surface of the reactor to be known continuously.

FIG. 1 is an illustration of a high-temperature permeation membrane reactor with weld seams of gold.

b) Analysis of the Gases

The reactant gases ($O_2$, $N_2$, $C_2H_6$) and the gases produced ($H_2$, $CH_4$, $CO_2$, $C_2H_4$, $C_2H_6$ and $H_2O$) were analysed using two chromatographs in a gaseous phase (GC), both of which are connected to a Chemstation HP in order to gather data and allow rapid analysis. The first GC (HP 5890 Series II) was equipped with a thermal conductivity detector (TCD) and a column 13X which allows the separation of $O_2$, $N_2$, $CH_4$, CO, and $H_2O$. $H_2$, $CH_4$, $CO_2$, $C_2H_4$, $C_2H_6$ and $H_2O$ were eluted from a HayeSep column on the second GC (Delsi Series 200) provided with a TDC.

Furthermore, argon was introduced with the reagents in order to readily determine a possible expansion of the flow owing to an increase in the number of moles during the process of DHOE. The balance in terms of carbon is in the order of 4%.

Gas leakages owing to a poor weld seam or incomplete densification of the membrane, should they occur, would thus be detected by following the concentration of nitrogen which allows the permselectivity in terms of $O_2$ to be calculated for the membrane reactor.

Example 1

Preparation of a Dense $Ba_{0.5}Sr_{0.5}CO_{0.8}Fe_{0.2}O_{3-\delta}$ Membrane Coated with Particles of VMgO a) Preparation of the Dense $Ba_{0.5}Sr_{0.5}CO_{0.8}Fe_{0.2}O_{3-\delta}$ Membrane The perovskite powder $Ba_{0.5}Sr_{0.5}CO_{0.8}Fe_{0.2}O_{3-\delta}$ (BSCFO) was prepared using a variant of the method commonly referred to as the "citrate method". In this method, the stochiometric quantities of $Ba(NO_3)_2$ (2.61 g; 0.5 eq), Sr(NO$_3$)$_2$ (2.11 g; 0.5 eq), Co(NO$_3$)$_2$6H$_2$O (4.65 g; 0.8 eq) and Fe(NO$_3$)$_3$6H$_2$O (4.05 mL of an aqueous solution at 0.988 mol/L; 8.76 g; 0.2 eq)(of purity >99.5%) were dissolved in 100 mL of distilled water followed by the addition of EDTA and citric acid at a molar ratio of perovskite, EDTA and citric acid equal to 1:1.5:3.

The violet coloured solution obtained was heated to a temperature of 100° C. until a gel-like material is obtained which is formed by evaporation of water after approximately three hours. The gel was then heated to 300° C. for three hours. The foam obtained was then calcined at 900° C. for four hours in air in order to lead to the production of a perovskite powder. This powder was then moulded in a mortar. Bare membrane discs were compressed at a pressure of 140 MPa for one minute. The densification of the discs was then carried out by means of sintering at 1150° C. for eight hours. The thickness of the membrane is from 1 mm+/−0.1 and the surface-area is 0.5 cm$^2$.

b) Preparation and Deposit of the Catalyst Particles VMgO

The particles based on mixed magnesium oxide doped using 10% by weight of vanadium were prepared from molecular precursors using the sol-gel method. This allows thin layers to be deposited which have high levels of purity and specific surface-area.

Figure 2:
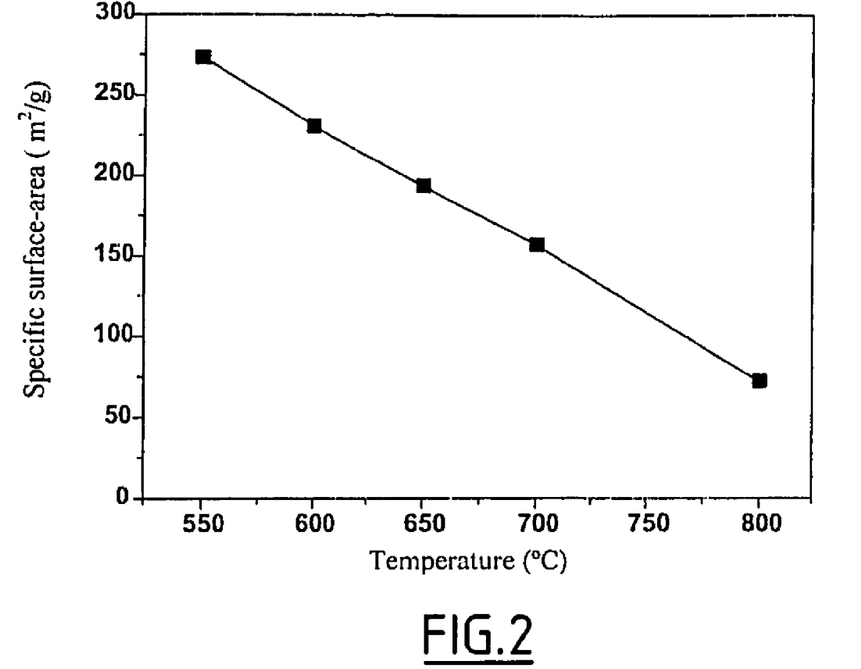
FIG. 2: Specific surface-area of the catalyst VMgO in accordance with temperature.

FIG. 2 illustrates the specific surface-area of VMgO in accordance with temperature.

The magnesium alkoxide used (Mg(OMe)$_2$) (9.34 g of Mg/L of methanol) was prepared by Epichem® and vanadium alkoxide (VO(OCH$_2$CH$_3$)$_3$ (208.8 g of V/L of methanol) is a solution marketed by Aldrich®. The two solutions were mixed so as to obtain a solution in which vanadium represents 10% by weight.

A few drops of the solution obtained, corresponding to a quantity of approximately 1 mg of VMgO were then deposited on the surface of the membrane using the technique of "spin-coating". The membrane was then placed directly in the reactor at 850° C. Particles of VMgO are thus obtained of 2 μm in size, which are distributed according to a density of [5.10$^6$ part/cm$^2$ (to within 10%)] and which cover approximately 40% of the surface-area of the membrane (to within 10%).

Figure 12:
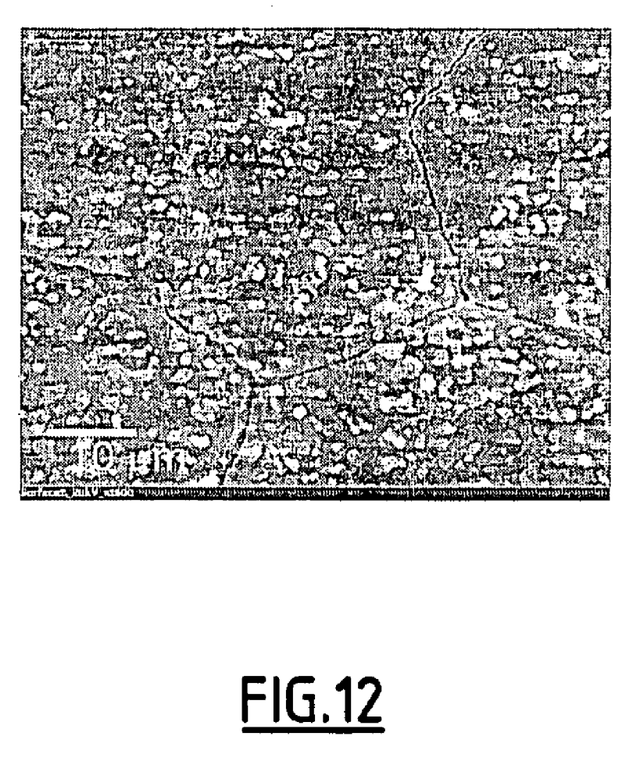
FIG. 12: Illustration of the surface of the membrane coated with dispersed particles of VMgO according to example 1 using electron scanning microscopy (Scale: 10 μm/cm).

FIG. 12 illustrates the surface of the membrane using electron microscopy (Scale: 10 μm/cm).

c) Features of the Powders

The formation of a pure perovskite structure was verified by means of X-ray diffraction.

The elemental composition was determined by ICP-OES (spectroflame) by analysing a sample dissolved by heating from 250° to 300° C. in a mixture of H$_2$SO$_4$ and HNO$_3$ after calcination.

TABLE 1

Cationic Composition of the BSCFO powder. Results of the ICP-OES analysis.

| Sample | Ba/at.-% | Sr/at.-% | Co/at.-% | Fe/at.-% |
|---|---|---|---|---|
| Batch 1 | 24.9 | 25.1 | 39.9 | 10.1 |
| Batch 2 | 25.0 | 25.0 | 40.0 | 10.0 |

Table 1 illustrates that this method ensures a very good reproducibility of the composition of the powder.

Example 2

Preparation of a Dense BSCFO Membrane Coated with Particles of Catalyst MgO

The dense Ba$_{0.5}$Sr$_{0.5}$Co$_{0.8}$Fe$_{0.2}$O$_{3-\delta}$ membrane is prepared in accordance with that of example 1.

The particles based on magnesium oxide were prepared using the sol-gel technique from a methanol-containing solution of Mg(OMe)$_2$ (Epichem®) at 9.34 g/L.

1 mg of the colloidal suspension obtained was deposited on the surface of the membrane using the technique of spin-coating. The membrane was then placed directly in the reactor at 850° C.

Particles of MgO are thus obtained of 2 μm in size, which are distributed according to a density of [5.10$^6$ part/cm$^2$ (to within 10%)] and which cover approximately 40% of the surface-area of the membrane.

Example 3

Dense BSCFO Membrane Coated with Particles of Pd Catalyst

The dense membrane used is in accordance with that described in example 1.

The Pd particles were deposited at the surface of the dense membrane in accordance with the technique of laser vaporisation. The laser ablation of a Pd bar of 99.99% purity (Goodfellow) was carried out using an Nd:YAG(BMI®) laser which is pulsed at 30 Hz and doubled in terms of frequency (532 nm).

The quantity of material deposited at the surface of the membrane was determined using a quartz microbalance (IN-FICON®).

Particles of Pd are thus obtained which have a mean size of 2-3 nm, which are distributed according to a density of 4.10$^{12}$ part/cm$^2$, and which cover approximately 8% of the membrane (to within 2%).

Figure 13:
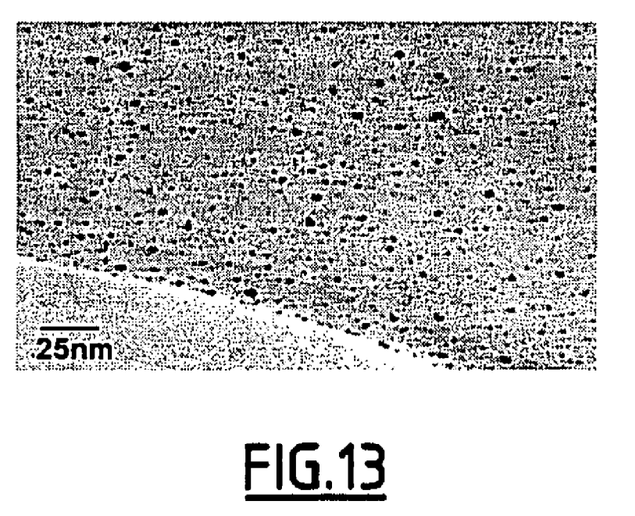
FIG. 13: Illustration of the surface of the membrane coated with dispersed particles of Pd according to example 3 using electron transmission microscopy (Scale: 25 μm/cm).

FIG. 13 is an illustration of the surface of the membrane coated with dispersed particles of Pd using electron microscopy.

Example 4

Determination of the Speed of Oxygen Permeation

Application of the membrane according to example 2 to the separation of oxygen.

Figure 3:
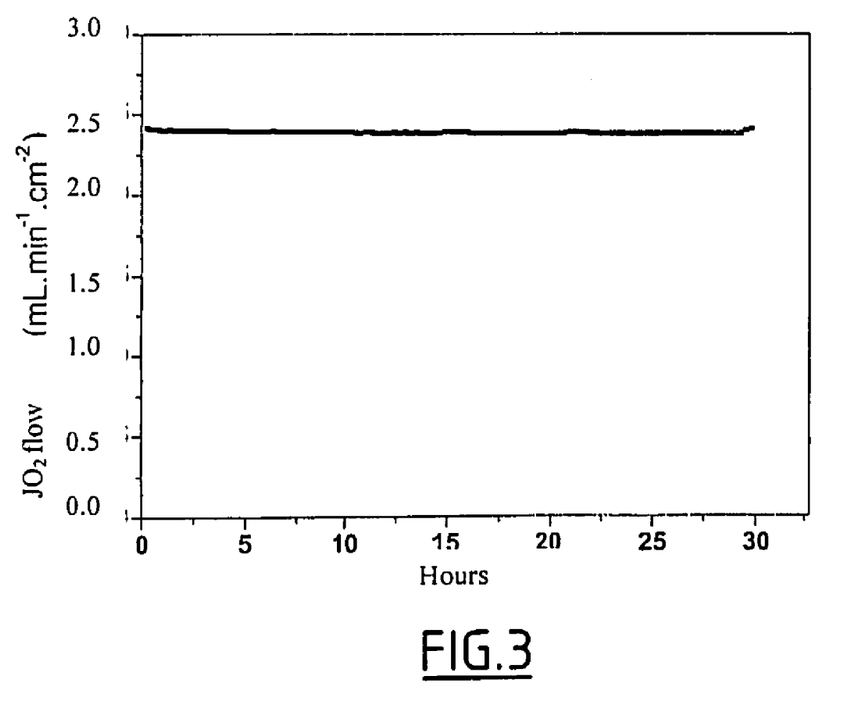
FIG. 3: Permeation flow of a $Ba_{0.5}Sr_{0.5}Co_{0.8}Fe_{0.2}O_{3-\delta}$ membrane which is coated with particles of MgO according to example 2 in accordance with time at 725° C.

The stability of the membrane of example 2 with regard to permeation of oxygen was examined by continuously recording the permeation flow at a constant partial pressure gradient of oxygen for 30 hours As described in FIG. 3, a stable permeation flow of oxygen of 2.4 mL·min·cm$^2$ is obtained at 725° C. These results represent a flow which is 1.5 times greater than that corresponding to the bare membrane.

Example 5

Application of the Membrane to the Oxidative Dehydrogenation of Ethane a) Main Possible Reactions $$C_2H_6 + \tfrac{1}{2}O_2 \rightarrow C_2H_4 + H_2O \quad \Delta rH°(750°C) = -93.927 \text{ kJ/mol} \quad (1)$$

$$C_2H_6 \rightarrow C_2H_4 + H_2 \quad \Delta rH°(750°C) = 144.022 \text{ kJ/mol} \quad (2)$$

$$H_2 + \tfrac{1}{2}O_2 \rightarrow H_2O \quad \Delta rH°(750°C) = -240 \text{ kJ/mol} \quad (3)$$

$$C_2H_6 \rightarrow CH_4 + H_2 + C \quad \Delta rH°(750°C) = 16.282 \text{ kJ/mol} \quad (4)$$

$$C + xO_2 \rightarrow CO/CO_2 \quad (5)$$

b) Calculation

Experiments for oxidation of ethane and propane in membrane reactors were carried out at different temperatures 700-825° C., different flow rates $C_2H_6$/He (35-65-100 mL/min) and at partial pressures of $C_2H_6$ of 0.25-0.44-0.55 atm at the side of the membrane which is in contact with ethane (oxidation zone).

All the calculations were carried out based on the partial pressure $P_x$, the total flow $F°_{ethane\ side}$, the expansion coefficient of the flow $C_{exp}$ and the surface-area of the active membrane S (based on the assumption of behaviour in accordance with the law for an ideal gas).

c) Effect of Temperature

Figure 4:
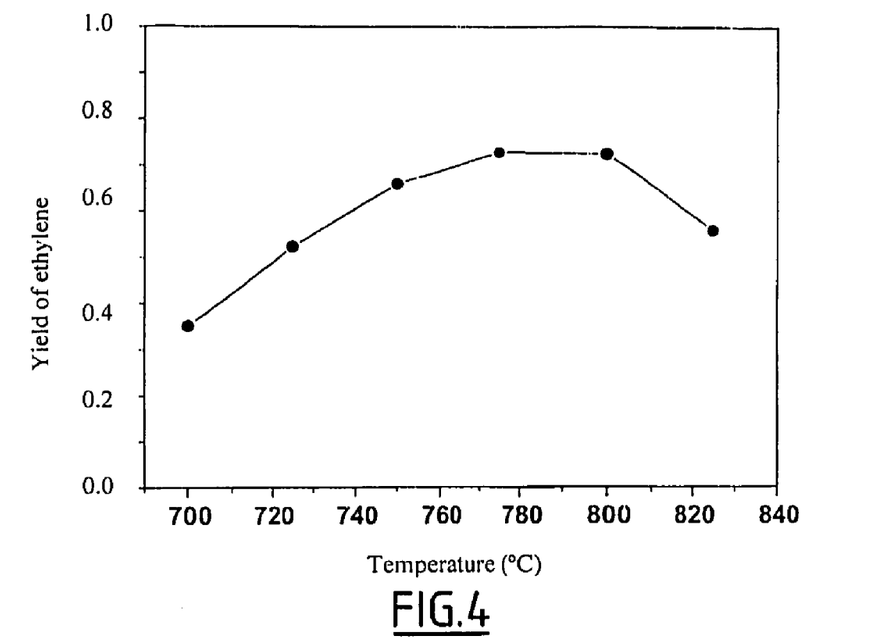
FIG. 4: Yield of ethylene in accordance with temperature obtained with a $Ba_{0.5}Sr_{0.5}Co_{0.8}Fe_{0.2}O_{3-\delta}$ membrane which is coated with particles of VMgO according to example 1.
Figure 5:
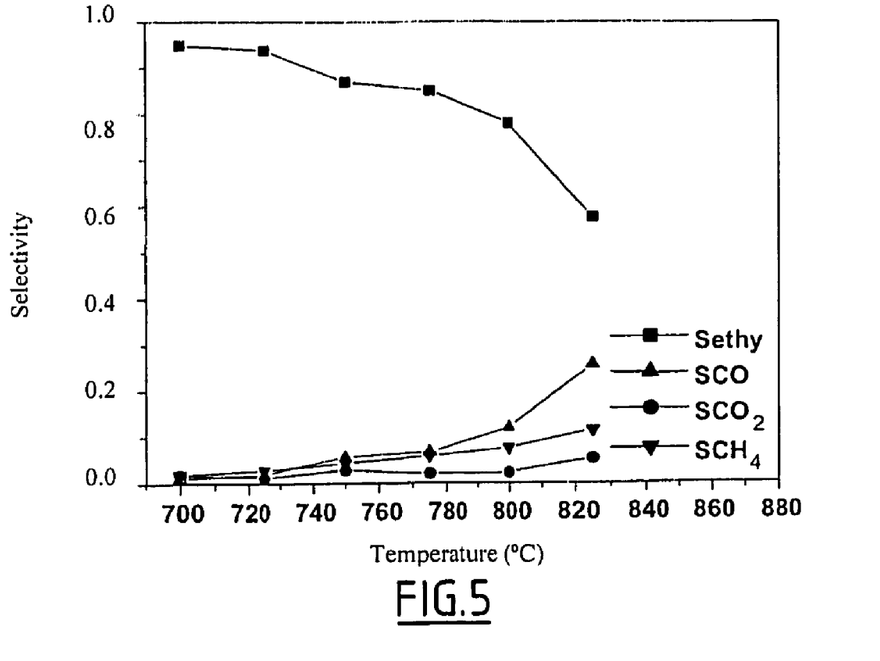
FIG. 5: Selectivity of the oxidative dehydrogenation reaction in accordance with temperature. Conditions: Reduction zone, $F_{AIR}$=50 mL/min, $P_{Air}$=1.2 bar; oxidation zone, $F_{C2H6/He}$= 37 mL/min, $P_{C2H6}$=0.25 atm.

FIG. 4 illustrates the yield of ethylene in accordance with temperature. This increases up to 775° C. in order to reach 75% (conversion=87%, selectivity=87%). At 700° C., the low yield (35%) is a result of a poor conversion (<40%) since the selectivity is greater than 90% as indicated in FIG. 5. However, at 825° C., the low yield (50%) is a result of a reduction of the selectivity of ethylene (<60%) in favour of carbon monoxide.

d) Effect of the Partial Pressure of Ethane

Figure 6:
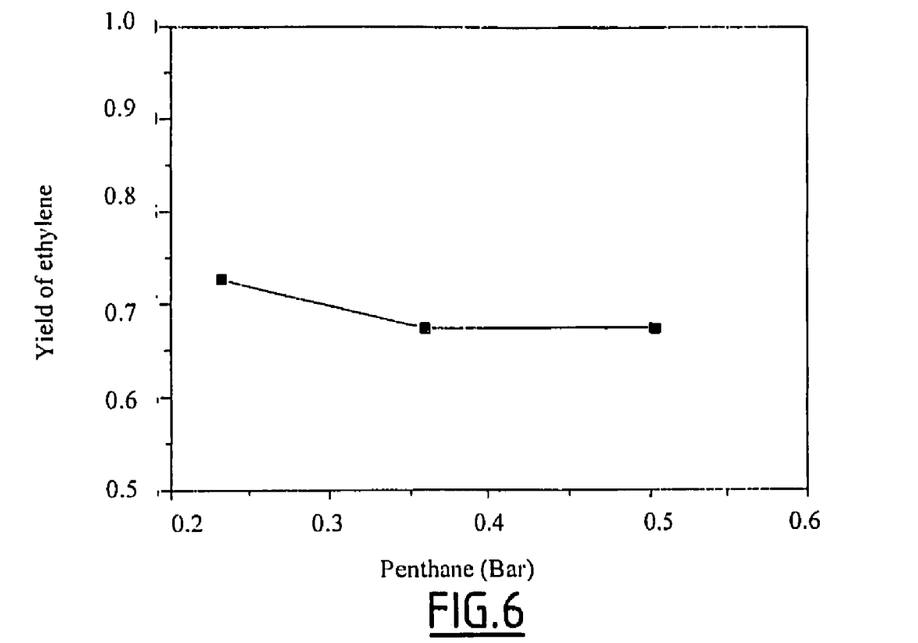
FIG. 6: Ethylene yield from the oxidative dehydrogenation reaction in accordance with the partial pressure of ethane. Conditions: Temperature=775° C. Reduction zone, $F_{AIR}$=50 mL/min, $P_{Air}$=1.2 bar; oxidation zone, $F_{C2H6/He}$=37 mL/min.

FIG. 6 illustrates the yield of ethylene in accordance with the partial pressure of ethane at the "optimum" temperature of 775° C. No variation of the yield in accordance with the partial pressure of ethane is seen. The selectivity and the conversion are also relatively constant.

Example 6

Figure 7:
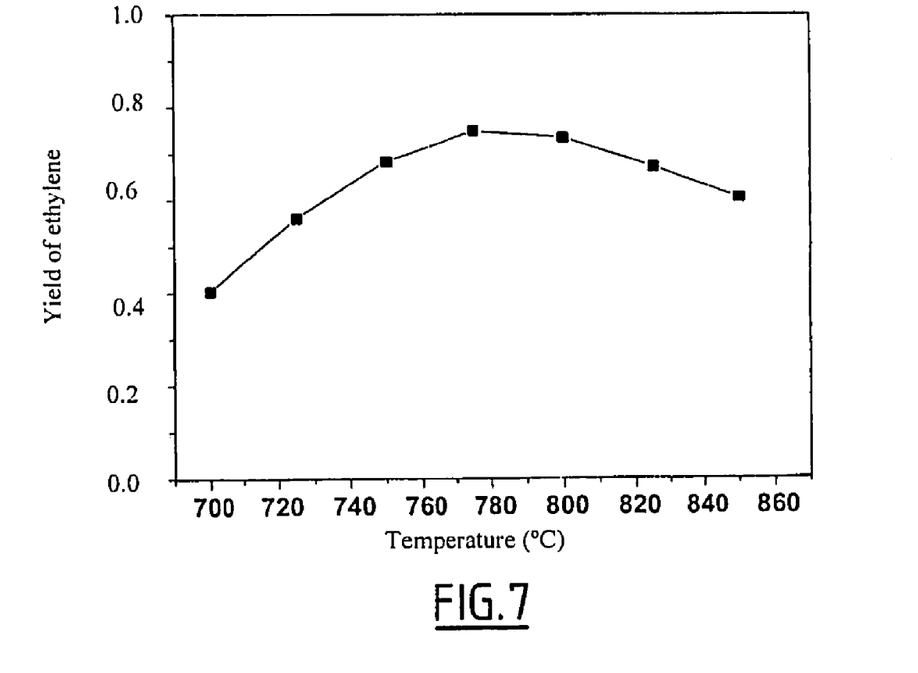
FIG. 7: Ethylene yield from the oxidative dehydrogenation reaction in accordance with temperature: Conditions: Reduction zone, $F_{AIR}$=50 mL/min, $P_{Air}$=1.2 bar; oxidation zone, $F_{C2H6/He}$=37 mL/min, $P_{C2H6}$=0.25 atm.

Application of Membranes According to Examples 1 to 3 to the Oxidative Dehydrogenation of Ethane FIG. 7 illustrates the ethylene yield of the membrane according to example 3 in accordance with temperature. This increases up to 775° C., in order to reach a maximum of 75%, which corresponds to a conversion rate of 87% and a selectivity rate of 87%.

Figure 8:
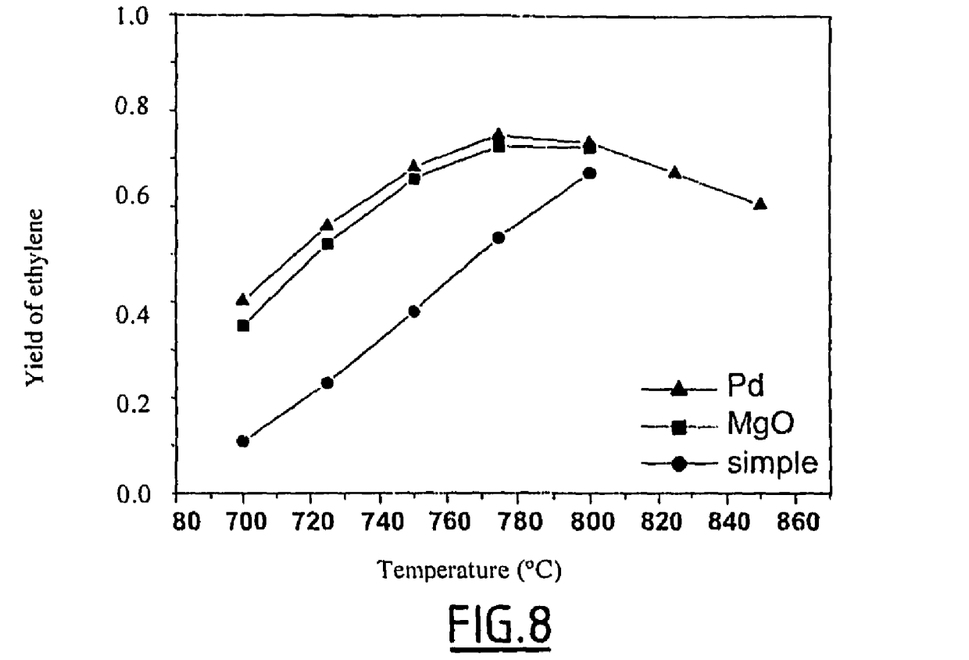
FIG. 8: Ethylene yield from the oxidative dehydrogenation reaction in accordance with the temperature using different catalysts. Conditions: Reduction zone, $F_{AIR}$=50 mL/min, $P_{Air}$=1.2 bar; oxidation zone, $F_{C2H6/He}$=37 mL/min, $P_{C2H6}$=0.25 atm.

FIG. 8 compares the ethane yields at different temperatures for dense membranes which are simple, that is to say, bare, and which are partially coated with dispersed particles based on magnesium oxide (examples 1 and 2) or Pd (example 3).

The presence of dispersed particles of Pd based on magnesium oxide allows a specific yield to be achieved at a temperature which is on average 75° C. lower than that of dense membranes.

The presence of dispersed particles of Pd or based on magnesium oxide in particular allows yields to be obtained which are greater than those of dense membranes (Y=75%, C=87%, S=87%) at a specific temperature.

The yields obtained with particles of catalyst based on magnesium oxide and Pd are comparable.

Example 7

Figure 9:
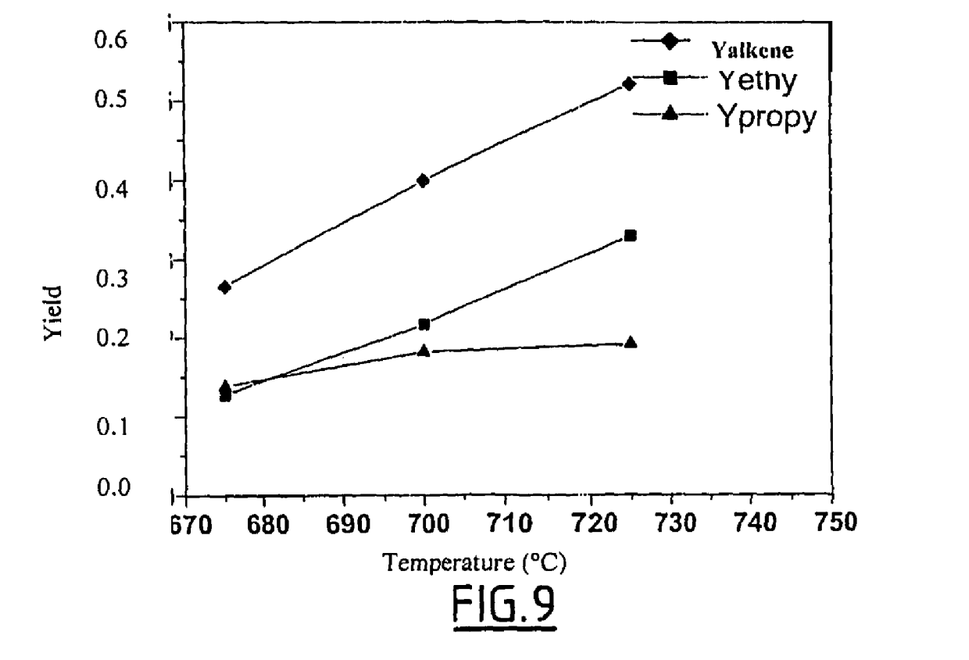
FIG. 9: Yield from the oxidative dehydrogenation reaction using a membrane according to example 2 in accordance with temperature. Conditions: Reduction zone, $F_{AIR}$=50 mL/min, $P_{Air}$=1.2 bar; oxidation zone $F_{C3H8/He}$=37 mL/min, $P_{C3H8}$=0.20 atm. Legend: Y alkene, Y ethy, Y propy represent the yields in terms of alkene, ethylene et propylene, respectively.

Application of the Membrane of Example 2 to the Oxidative Dehydrogenation of Propane a) Effect of Temperature FIG. 9 indicates the yields of propylene, ethylene and total alkene (i.e. propylene and ethylene) in accordance with temperature. For propylene, a maximum yield of 19% (S=27.4%, C=69.7%) is obtained at 725° C. This low yield is principally the result of a secondary cracking reaction of the propane under the operating temperature conditions of the membrane. The main product obtained is ethylene (S=47.2% at 725° C.), which is a very valuable product.

b) Effect of the Partial Pressure of Propane

Figure 10:
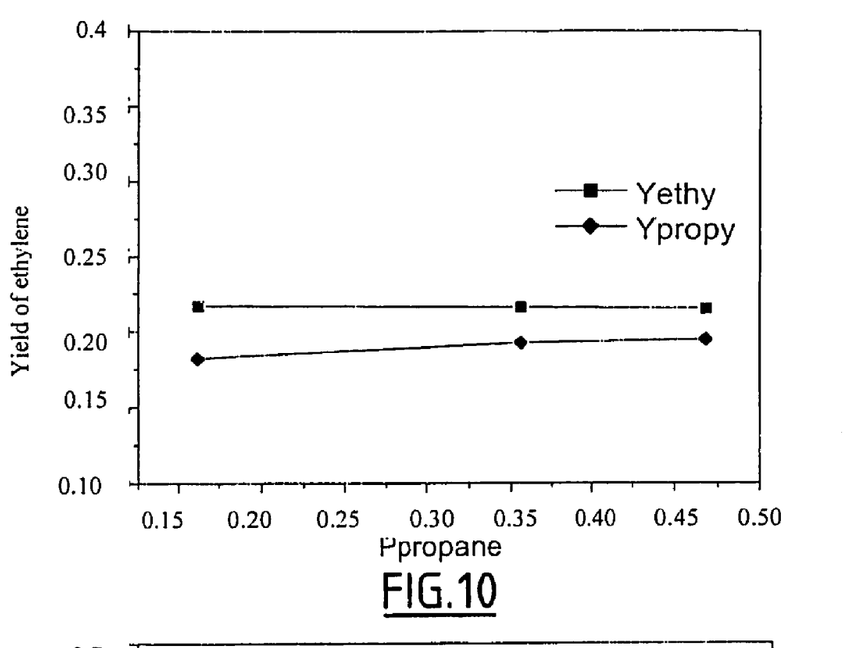
FIG. 10: Yield from the oxidative dehydrogenation reaction using a membrane according to example 2 in accordance with the partial pressure of propane. Conditions: Temperature=700° C. Reduction zone, $F_{AIR}$=50 mL/min, $P_{Air}$=1.2 bar; oxidation zone, $F_{C3H8/He}$=34 mL/min.

FIG. 10 illustrates the yield of propylene and ethylene at 700° C. in accordance with the partial pressure of propane.

The yield in terms of ethylene and propylene remains constant for a partial pressure in terms of propane of between 0.15 and 0.50 bar.

Example 8

Figure 11:
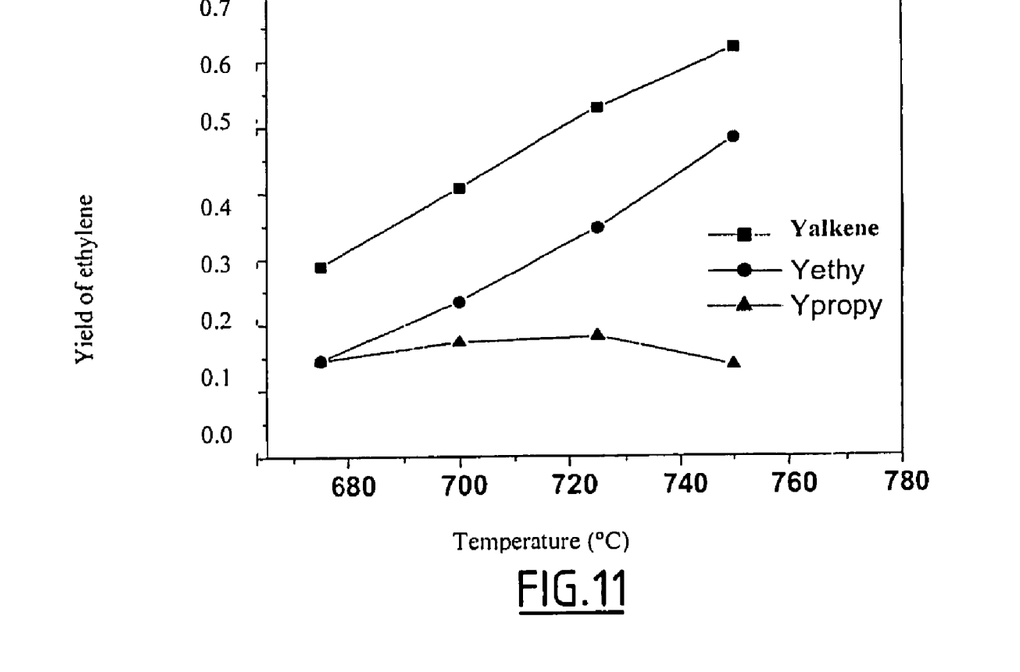
FIG. 11: Yield from the oxidative dehydrogenation reaction in accordance with temperature using a membrane according to example 3. Conditions: Reduction zone, $F_{AIR}$=50 mL/min, $P_{Air}$=1.2 bar; oxidation zone, $F_{C3H8/He}$=37 mL/min, $P_{C3H8}$=0.20 atm.

Application of the Membrane of Example 3 to the Oxidative Dehydrogenation of Propane FIG. 11 indicates the yields of propylene, ethylene and alkene (propylene and ethylene) in accordance with the temperature. For propylene, a maximum yield of 18.2% (S=25.9%, C=70.1%) is obtained at 725° C.

Example 9

Comparative Study of the Membranes of Examples 1, 2 and 3 and the Membranes of the Prior Art The permeation flows of oxygen of various membranes were determined using the reactor described in FIG. 1 under the conditions indicated in the above section "Material and methods".

These results indicate that the modification of one of the surfaces of the dense membrane using particles of noble metals or based on magnesium oxide allows the permeation flow of oxygen to be significantly increased.

TABLE 2

| Membrane | T (° C.) | Flow of oxygen | Reference |
|---|---|---|---|
| Without surface-area modification | 800 | Mol cm$^{-2}$s$^{-1}$ 6.69E−07 | [1] |
| $Ba_{0.5}Sr_{0.5}Co_{0.8}Fe_{0.2}O_x$ | 800 | 3.12E−07 | [2] |
| $BaBi_{0.4}Co_{0.2}Fe_{0.4}O_{3-\&}$ | 800 | 1.12E−07 | [3] |
| $La_{0.2}Sr_{0.8}Co_{0.2}Fe_{0.8}O_{3-\&}$ | 800 | 1.86E−08 | [4] |
| $La_{0.6}Sr_{0.4}Co_{0.2}Fe_{0.8}O_{3-\&}$ | 800 | 5.20E−08 | [5] |
| $La_{0.6}Sr_{0.4}CO_{0.8}Fe_{0.2}O_{3-\&}$ | 800 | 4.80E−07 | [1] |
| $SrCo_{0.8}Fe_{0.2}O_{3-\&}$ | 800 | 3.35E−07 | [7] |
| $BaCo_{0.4}Fe_{0.4}Zr_{0.2}O_{3-1}$ | 800 | 1.58E−08 | [8] |
| $Bi_2V_{0.8}Mn_{0.2}O_{5.3}$ | 800 | 1.00E−06 | Example 2 |
| With surface-area modification | | | |

TABLE 2-continued

| Membrane | T (° C.) | Flow of oxygen | Reference |
|---|---|---|---|
| $Ba_{0.5}Sr_{0.5}Co_{0.8}Fe_{0.2}O_x$ + MgO | | | |
| Ibid + Pd | 800 | 1.12E−06 | Example 3 |
| Ibid + VMgO | 800 | 1.27E−06 | Example 1 |

1. Shao, Z., et al., *Investigation of the permeation behavior and stability of a Ba0.5Sr0.5Cu0.8Fe0.2O3-[delta] oxygen membrane*. Journal of Membrane Science, 2000. 172(1-2): p. 177-188.
2. Shao, Z., et al., *Synthesis and oxygen permeation study of novel perovskite-type BaBixCo0.2Fe0.8-xO3-.delta. ceramic membranes*. J. Membr. Sci., 2000. 164(1-2): p. 167-176.
3. Li, S. G., et al., *Comparison of oxygen permeability and stability of perovskite type La(0.2)A(0.8)Co(0.2)Fe(0.8)O (3-delta) (A=Sr, Ba, Ca) membranes*. Industrial and Engineering Chemistry Research, 1999. 38(8): p. 2963-2972.
4. Lee, S., et al., *Oxygen-permeating property of LaSrBFeO3 (B=Co, Ga) perovskite membrane surface-modified by LaSrCoO3*. Solid State Ionics, 2003. 158(3-4): p. 287-296.
5. Teraoka, Y., et al., *Catalytic effects in oxygen permeation through mixed-conductive LSCF perovskite membranes*. Solid State Ionics, 2002. 152-153: p. 681-687.
6. Qiu, L., Lee T. H., *Oxygen permeation studies of SrCo0.8Fe0.2O3-&*. Solid State Ionics, 1995. 76: p. 321-329.
7. Tong, J., et al., *Investigation of ideal zirconium-doped perovskite-type ceramic membrane materials for oxygen separation*. Journal of Membrane Science, 2002. 203(1-2): p. 175-189.
8. Yang, Y. L., Qiu L. Jacobson, *Manganese doped bismuth vanadate solid electrolytes: oxygen permeation in Bi2V0.8Mn0.2O5.3*. Journal of Materials Chemistry, 1997. 7: p. 937-941.

The invention claimed is:

1. An oxygen conducting membrane, comprising:
 a mixed conducting dense membrane of multimetal oxide, one surface of which is covered with dispersed particles containing magnesium oxide or noble metals, wherein the mixed conducting dense membrane is a layer comprising a multimetal oxide compound having a formula:

$$Ba_xSr_{1-x}Co_{1-y}Fe_yO_{3-z}$$

where $0 \leq x \leq 1$,
 $0 \leq y \leq 1$, and
 z is a number which renders a charge of the compound neutral and which defines oxygen deficiency, and
 the particles based on magnesium oxide or noble metals represent from 0.01 to 0.1% by weight of the dense membrane.

2. The membrane according to claim 1, in which the particles containing magnesium oxide or noble metals have a diameter of between 5 and 3000 nm.
3. The membrane according to claim 1, in which the mixed conducting dense membrane of multimetal oxide has a perovskite structure.
4. The membrane according to claim 1, in which the multimetal oxide comprises $Ba_{0.5}Sr_{0.5}Co_{0.8}Fe_{0.2}O_{3-z}$.
5. The membrane according to claim 1, in which the mixed conducting dense membrane of multimetal oxide has a thickness of between 0.5 and 10 mm.
6. The membrane according to claim 1, in which the particles are containing magnesium oxide.
7. The membrane according to claim 6, in which the particles containing magnesium oxide are doped using vanadium.
8. The membrane according to claim 1, in which the particles are particles of noble metals or alloys thereof.
9. The membrane according to claim 1, in which the noble metals are selected from the group consisting of Pd, Pt, Rh, Ag, Au, Ru and Ir.
10. A method for preparing the oxygen conducting membrane as defined according to claim 1, comprising:
 a) providing the mixed conducting dense membrane;
 b) preparing a colloidal suspension containing the magnesium oxide in an organic solvent;
 c) placing the suspension obtained in contact with the mixed conducting dense membrane; and
 d) calcining the membrane obtained.
11. A method for preparing the oxygen conducting membrane as defined according to claim 1, comprising:
 a) providing the dense membrane of multimetal oxide; and
 b) depositing the particles of noble metals or alloys thereof by means of laser vaporisation.
12. A membrane reactor comprising an oxidation zone and a reduction zone which are separated by the oxygen conducting membrane as defined in claim 1.
13. The membrane reactor according to claim 12, in which the oxidation zone is in contact with the surface of the membrane coated with dispersed particles containing magnesium oxide or noble metals.
14. A method for oxidising a reactant gas, comprising:
 i) providing the membrane reactor according to claim 12;
 ii) introducing the reactant gas into the oxidation zone;
 iii) introducing the gas containing oxygen into the reduction zone; and
 iv) heating the membrane which separates the oxidation and reduction zones to an operating temperature.
15. The method according to claim 12, in which the reactant gas is a light hydrocarbon which is oxidised into alkene.
16. The method according to claim 12, in which the light hydrocarbon is ethane which is oxidised into ethylene.

* * * * *